US006293223B1

(12) United States Patent
Blossey et al.

(10) Patent No.: US 6,293,223 B1
(45) Date of Patent: Sep. 25, 2001

(54) ARTIFICIAL DIET AND METHOD USING AN ARTIFICIAL DIET, FOR MASS REARING OF INSECTS

(75) Inventors: Bernd Blossey, Groton, NY (US); Debra Eberts, Evergreen, CO (US)

(73) Assignees: Cornell Research Foundation, Inc., Ithaca, NY (US); The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/573,886

(22) Filed: May 19, 2000

(51) Int. Cl.[7] ............................. A01K 29/00; A23L 3/005
(52) U.S. Cl. .................................. 119/6.5; 426/2
(58) Field of Search ................. 119/6.5, 6.6; 426/2; 449/1, 2

(56) References Cited

U.S. PATENT DOCUMENTS

| | | | |
|---|---|---|---|
| 3,488,196 | 1/1970 | Niimura et al. | 426/2 |
| 3,583,871 | 6/1971 | Niimura et al. | 426/2 |
| 4,484,539 | 11/1984 | Nettles et al. | 119/6.6 |
| 4,840,800 | 6/1989 | Harris | 426/2 |
| 5,178,094 * | 1/1993 | Carr et al. | 119/6.5 |
| 5,351,643 | 10/1994 | Hughes | 119/6.5 |
| 5,799,607 | 9/1998 | Greany et al. | 119/6.5 |
| 5,834,177 | 11/1998 | Cohen | 435/1.1 |
| 5,899,168 | 5/1999 | Rojas et al. | 119/6.5 |
| 5,927,004 * | 7/1999 | Stocker | 119/6.5 |
| 5,945,271 | 8/1999 | Cohen | 435/1.1 |
| 6,129,935 * | 10/2000 | White et al. | 119/6.5 |

OTHER PUBLICATIONS

Hunt, D. W. A., et al., Journal of Economic Entomology 85, No. 5, 1837–1877 (10/92).
Blossey, B., et al., Journal of Economic Entomology 92, No. 2, 325–334 (4/99).

* cited by examiner

*Primary Examiner*—Charles T. Jordan
*Assistant Examiner*—Elizabeth Shaw

(57) ABSTRACT

A diet for mass rearing of insects that feed on hard, woody plant tissue, e.g., beetles including weevils that feed on hard, woody plant tissue, comprises a homogeneous mixture of first portion which is subjected to sterilization in an autoclave comprising water, agar and salt mix and optionally also yeast extract, casein and a sugar, and of a second portion which is not subjected to sterilization in an autoclave which comprises host plant part fed on by insect larvae, vitamin mix, and antimicrobial agent(s). A method for mass rearing of insects that feed on hard, woody plant tissue, e.g., weevils, e.g., *Hylobius transversovittatus* or *Cyphocleonos achates* Fahraeus, comprises placing first instar insect larvae on an artificial diet comprising ground host plant part, incubating the larvae on the diet in darkness at a temperature ranging from 15 to 30° C. and a relative humidity ranging from 50 to 90%, and retrieving adults as they emerge.

12 Claims, No Drawings

ARTIFICIAL DIET AND METHOD USING AN ARTIFICIAL DIET, FOR MASS REARING OF INSECTS

The invention was made at least in part with United States Government support under a collaborative agreement with the Bureau of Reclamation. No grant number is associated with the support. A requisition request number given by the Bureau of Reclamation was #5-8220-0081-00060 and an order number given by the Bureau of Reclamation was #1425-5-AA-81-20650. The United States Government has certain rights in the invention.

TECHNICAL FIELD

The invention in one aspect is directed to a diet for mass rearing of insects that feed on hard, woody plant tissue. The invention in another aspect is directed to a method of mass rearing of insects that feed on hard, woody plant tissue, for example, to a method of mass rearing of the root-boring weevil *Hylobius transversovittatus* Goeze for use as biological control agent of *Lythrum salicaria* L. or to a method of mass rearing of the root-boring weevil *Cyphocleonus achates* Fahraeus for use as a biological control agent of *Centaurea maculosa* L.

BACKGROUND OF THE INVENTION

Purple loosestrife (*Lythrum salicaria* L., Lythraceae), a Eurasian perennial wetland plant, was introduced into North America in the early 1800's. Negative impacts on biodiversity of infested wetlands and the inability of chemical, physical or mechanical means to provide long-term control resulted in the importation and release of host-specific phytophagous insects from the native range of the plant, a classical biological weed control program. Of nine host-specific insects species considered as control agents, three (the two leaf feeders *Galerucella calmariensis* L., and *G. pusilla* Duftschmidt [Coleoptera: Chrysomelidae] and a root feeder *Hylobius transversovittatus* Goeze [Coleoptera: Curculionidae]) were introduced into North America in 1992. An additional species that attacks the flowers (*Nanophyes marmoratus* Goeze [Coleoptera: Curculionidae]) was introduced in 1994.

Because as much as 60% of the annual biomass production of *L. salicaria* is stored below-ground and rootstocks of over 1 kg fresh biomass are common in mature plants, the root-feeding weevil *Hylobius transversovittatus* is considered a very important one of the host-specific insect species introduced and a prime candidate as a biological control agent. Attack by *H. transversovittatus* reduces flowering period, plant height, and plant biomass and changes biomass allocation patterns resulting in reduced performance of purple loosestrife.

It has been rather difficult to establish viable field populations of *H. transversovittatus*. The low abundance of this species in Europe prevented field collections for release in North America. Adults for initial introductions in 1992 were offspring of weevils collected across Europe. Larvae were reared on potted plants (of purple loosestrife) in a common garden in Germany. A total of 1,331 adults and 30,830 eggs were released in nine states and two Canadian provinces through 1993 and initial establishment was confirmed. Rearing of *H. transversovittatus* has continued at Cornell University and to a lesser extent at facilities of the Bureau of Reclamation in Denver, since 1993. This has allowed the distribution of eggs for field release despite the low number of adults. Although well over 100,000 eggs were distributed by 1999, field establishment rates appear rather low.

Increasing the availability of adults for field release has been considered crucial to increase field populations of the weevil to avoid negative effects due to inbreeding in small populations which could jeopardize the biological control program targeting *L. salicaria*.

SUMMARY OF THE INVENTION

One goal of the invention was to achieve field establishment of *H. transversovittatus* through mass rearing of larvae on an artificial diet and subsequent field release of adults and to produce individuals at lower costs and faster than would be possible from allowing natural population build-up in the field or relying on natural hosts in a common garden. This has resulted in the development of a diet for mass rearing of insects that feed on hard, woody plant tissue which includes the host plant part fed on by larvae of the insect and water and agar ingredients in amounts to provide a gel to hold the host plant part and other ingredients together in homogeneous admixture, and in the development of a method of mass rearing of insects that feed on hard, woody plant tissue including the development of a method for the mass rearing of the root-boring weevil *Hylobius transversovittatus* for use, for example, as a biological control agent of *Lythrum salicaria* and the development of a method of mass rearing of the root-boring weevil *Cyphocleonus achates* Fahraeus for use, for example, as a biological control agent of *Centaurea maculosa* L.

In one embodiment, the invention is directed to a diet for mass rearing of insects that feed on hard, woody plant tissue, comprising a homogeneous mixture of a first portion which is subjected to sterilization in an autoclave comprising water and agar in amounts to form a gel containing the other diet components and a nutrition providing effective amount of salt mix, and of a second portion which is not subjected to sterilization in an autoclave, said second portion comprising a larval development effective formulation compatible amount of ground host plant part fed on by larvae of the insects, a nutrition providing effective amount of vitamin mix, and a pathogen growth suppressing amount of antimicrobial agent(s).

In another embodiment, the invention is directed to a method of mass rearing of insects that feed on hard, woody plant tissue comprising the steps of: (a) placing first instar insect larvae on an artificial diet comprising ground host plant part fed on by the larvae; (b) incubating the larvae on the diet at a temperature of 15 to 30° C. and a relative humidity of 50 to 90%; and (c) retrieving adults as they emerge. The method of this embodiment can be used, for example, for mass rearing of the root boring weevil *Hylobius transversovittatus*, for use as a biological control agent of *Lythrum salicaria*, and in such case first instar *Hylobius transversovittatus* larvae are used in step (a), and the artificial diet of step (a) comprises ground purple loosestrife root. The method of this embodiment can also be used, for example, for mass rearing of the root-boring weevil *Cyphocleonus achates* Fahraeus, for use as a biological control agent of *Centaurea maculosa* L., and in such case first instar *Cyphocleonus achates* Fahraeus larvae are used in step (a), and the artificial diet of step (a) comprises ground *Centaurea maculosa* L. root or ground *Centaurea diffusa* root.

The term "host plant" is used herein to mean the plant species associated with larval development in the field. The insect species to which the invention herein pertains have developed exclusive relationships with a single or a few select plant species which are referred to by those skilled in the art as host plants. Larval development can only be completed on these host plants, and females will restrict their oviposition to host plants allowing larval development. Attacked plant parts can be stems, roots, wood, etc., depending on the species. In any rearing, the host plant part fed upon in the field by the larvae should be used in the diet.

The term "formulation compatible" is used herein to mean allowing formulation of a homogeneous mix and/or to allow pourability during formulation and positioning of the diet.

DETAILED DESCRIPTION

We turn now to the embodiment herein directed to a diet for mass rearing of insects that feed on hard, woody tissue. The diet is preferably for rearing of beetles including weevils, from larvae. The diet comprises a homogeneous mixture of a first portion which is subjected to sterilization in an autoclave comprising water and agar in amounts to form a gel containing the other diet components and a nutrition providing effective amount of salt mix, and of a second portion which is not subjected to sterization in an autoclave comprising a larval development effective formulation compatible amount of ground host plant part fed on by larvae of the insects, a nutrition providing effective amount of vitamin mix and a pathogen growth suppressing amount of antimicrobial agents.

Preferably, the diet has a first portion comprising by weight of the diet of 0.01 to 5% salt mix and a second portion comprising by weight of the diet of 0.1 to 40% ground host plant part and 0.01 to 5% vitamin mix and for the antimicrobial agent(s) 0.01 to 5% sorbic acid and 0.01 to 5% methyl paraben.

Typically the first portion comprises by weight of the diet from 5 to 70% water and from 0.5 to 10% agar.

Preferably the first portion also comprises by weight of the diet from 1 to 25% protein nutrients and from 0.5 to 15% of a sugar, and very preferably the protein nutrients consist by weight of the diet of 0.5 to 10% yeast extract and from 0.5 to 15% casein.

A very preferred diet for mass rearing of weevils has a first portion comprising by weight of the diet from 55 to 70% water, 1 to 5% agar, 1 to 5% yeast extract, 1 to 5% sucrose, 0.1 to 2% salt mix, and 1 to 5% casein; and a second portion comprising by weight of the diet from 20 to 30% or from 20 to 25% ground host plant part, 0.1 to 2% vitamin mix, 0.05 to 1% sorbic acid, and 0.05 to 1% methyl paraben.

The diet is generally applicable to insects that feed on hard, woody plant tissue including beetles, e.g., weevils and long-horned beetles (Cerambycids), that feed on hard, woody plant tissue. These include, for example, root feeding, stem and wood boring and bark and stump feeding species. The root feeding species include, for example, the weevils *Hylobius transversovittatus* Goeze and *Cyphocleonus achates* Fahraeus. The stem and wood boring species include, for example, the long-horned beetles *Megacyllene robiniae* Forster, or *Saperda cretata* Newman. The bark and stump feeding species include, for example, other species in the genus Hylobius, e.g., *Hylobius pales* Herbst and *Hylobius radicis* Buchanan and the weevil *Pissodes nemorensis* Germar.

In one case, the diet is for mass rearing of *Hylobius transversovittatus*, for use, for example, as a biological control agent of *Lythrum salicaria*, and the ground host plant part is purple loosestrife root.

In another case, the diet is for mass rearing of *Cyphocleonus achates* Fahraeus, for use, for example, as a biological control agent of *Centaurea maculosa* L., and the ground host plant part is selected from the group consisting of ground *Centaurea maculosa* root and ground *Centaurea diffusa* root.

As indicated above, certain of the diet components are subjected to sterilization in an autoclave and others of the diet components are not subjected to sterilization in an autoclave. The diet components that can be sterilized in an autoclave without loss of their activity and biological function are subjected to such sterilization and a purpose of this is to remove any potential for contamination, for example, by fungi or bacteria. Thus, water, agar, yeast extract, sugar, salt mix and casein diet components are autoclaved because they can be autoclaved without loss of activity or biological function. On the other hand, the host plant parts, vitamins, sorbic acid and methyl paraben cannot be autoclaved without loss of activity or biological function and are in the group of diet components not subjected to autoclaving. The sterilization in an autoclave is readily carried out by placing the ingredients to be sterilized in open containers in the autoclave, filling the autoclave with water to the indicated point for the production of steam for sterilization, and then heating, for example, at 200 to 300° C. at a pressure ranging from 5 to 20 psi for example, for 20 minutes, to steam sterilize the diet components in the autoclave.

The inclusion of host plant part in the diet composition causes an increase in the number of adults emerging from larvae incubated on the diet with the percentage of adults emerging increasing as the plant part percentage in the diet is increased to about 25% of the diet. A preferred weight percentage of host plant part in the diet is 12 to 30%, more preferably from 20 to 30% or 20 to 25%. The part of the host plant used is that fed on in the field by larvae of the insect for which the diet is intended. The host plant part for mass rearing of the root-boring weevil *Hylobius transversovittatus* is purple loosestrife (*Lythrum salicaria*) root. To produce *Cyphocleonus achates* Fahraeus, a root feeding biocontrol agent of spotted knapweed, *Centaurea maculosa* L., the host plant part is root of *Centaurea maculosa* (spotted knapweed) or *Centaurea diffusa* (diffuse knapweed). The roots are available from harvesting from host plant. For example, purple loosestrife roots can be excavated at any wetland containing the species, e.g., at Martens Marsh in Savannah, N.Y. or from the Federal Correction Institution at Lakewood, Colo. *Centaurea maculosa* roots can be harvested at grasslands infested with the species, e.g., in areas around Fort Drum, N.Y. *Centaurea diffusa* roots can be harvested at grasslands infested with the species, e.g., around Grand Coulee Dam in Washington State. Using ground host plant part instead of plant parts which are not ground, allows producing a homogeneous mix. Ground root is obtained, for example, by washing harvested root, removing dead parts and woody shoots, sterilizing using bleach, rinsing, shredding, and then grinding, e.g., using a Fritsch P-15 cutting mill or similar device, e.g., to a coarse powder that will pass through a 1–2 mm size screen. Once the plant material is ground, it is preferably frozen if not going to be used within a few hours, e.g., at −70° C., since there is a high incidence of bacteria/fungal contamination when the plant material is allowed to remain at room temperature for more than a few hours.

We turn now to the agar and water ingredients. Agar is included as a gelling substance and acts as a kind of glue to keep all the other ingredients together, i.e., to form a gel of the entire mixture. The water interacts with the agar so that a gel is formed in which the ground host plant part and other ingredients are held in homogenous admixture. The goal is to adjust agar and water amounts to achieve a mixture which when it cools down is solid, yet sufficiently soft to allow larval development. Good results have been obtained when the agar and water are utilized in amounts so the ultimate formulation has a consistency similar to that of chunky peanut butter. An agar used in the work herein was obtained from Sigma Chemicals (St. Louis, Mo.) under item #A9915.

We turn now to the salt mix ingredient. This ingredient is to supply minerals in the diet as essential building blocks for cells and tissue. Those salt mixes typically used in insect rearing are suitable for use herein. These include Wesson's salt mix containing non-hydrated ferric orthophosphate rather than hydrated ferric phosphate and Beck's salt mix. Use of Beck's salt mix with hydrated ferric orthophosphate rather than non-hydrated ferric orthophosphate resulted in increased contamination and much longer larval development times. Use of Wesson's salt mix with non-hydrated ferric orthophosphate was found to provide a significantly lower incidence of adult deformities than use of Beck's salt mix. The composition of Wesson's salt mix is set forth below.

TABLE 1

| Component | g/kg |
|---|---|
| Calcium phosphate tribasic | 149.0 |
| Calcium carbonate | 210.0 |
| Magnesium sulfate 7 $H_2O$ | 90.0 |
| Aluminum potassium sulfate 12 $H_2O$ | 0.09 |
| Cupric sulfate 5 $H_2O$ | 0.39 |
| Ferric phosphate | 14.7 |
| Manganese sulfate | 0.2 |
| Potassium chloride | 120.0 |
| Potassium phosphate monobasic | 310.0 |
| Potassium iodide | 0.05 |
| Sodium fluoride | 0.57 |
| Sodium chloride | 105.0 |

Wesson's salt mix containing non-hydrated ferric orthophosphate is available from Sigma Chemicals under #W1374. Beck's salt mix is available from Bioserve (Frenchtown, N.J.) under catalog number F8537.

We turn now to the optional protein nutrients, e.g., yeast extract and casein.

We turn now to the optional yeast extract ingredient. It is a nutrient source for the larvae. It is obtained, for example, by extracting from the yeast used in breweries and bakeries. It is a standard ingredient in most insect artificial diets. Yeast extracts are described, for example, in Kirk-Othmer Encyclopedia of Chemical Technology, 2d edition, John Wiley & Sons (1970), Vol. 22, page 531, which is incorporated herein by reference. Suitable yeast extract ingredients were obtained from Sigma Chemicals under item numbers Y1000 and 0500.

We turn now to the optional casein ingredient. This is another ingredient which is a source of nutrients and is typically used in insect rearing. The casein used in the experiments of the invention was obtained from Sigma Chemicals under item number C7078.

We turn to the optional sugar ingredient. It fosters larval development. Suitable sugars include, for example, sucrose, and fructose. Maximum benefit has been obtained when sucrose is used and amounted to about 2.5% of diet, e.g., 2.4 to 2.6% of diet. Any common form of sucrose is suitable including that sold in grocery stores.

We turn now to the vitamin mix ingredient. As in humans, vitamins are necessary for insects. Vitamin mixes are standard ingredients in most insect artificial diets, and those vitamin mixes typically used for insect rearing are useful in the diets herein. Suitable vitamin mixes are set forth in Table 2 below.

TABLE 2

| Ingredient | Quantity (in grams) Mix 1 | Quantity (in grams) Mix 2 |
|---|---|---|
| D-Biotin | 0.02 | 0.02 |
| Choline Chloride | 75.0 | 50.0 |
| Folic Acid | 0.9 | 0.25 |
| Myo-Inositol | 5.0 | 20.0 |
| D-(+)-Glucose | | 646.73 |
| Niacinamide | 4.6 | 1.0 |
| D-Pantothenic Acid | 3.0 | 1.0 |
| Pyridoxine HCl | 1.0 | 0.25 |
| Riboflavin | 1.0 | 0.25 |
| Tocopherol | 5.0 | 8.0 |
| Thiamine HCl | 1.0 | 0.25 |
| Vitamin $B_{12}$ | 0.0135 | 2.0 |
| L-Ascorbic Acid | 45 | 270 |
| Menadione | 2.25 | |
| Para-aminobenzoic Acid | 5.0 | |
| Vitamin A concentrate | 4.5 | |
| Vitamin D concentrate | 0.25 | |

Mix 1 is based on a published diet and needs to be custom mixed. Mix 2 is Vanderzant mix and is obtainable from Sigma Chemicals under item number V1007. There were no significant differences in larval development time or proportion of adults emerging between the two vitamin mixes in experiments conducted involving use of the diet for mass rearing of *Hylobius transversovittatus*.

We turn now to the antimicrobial ingredient(s). These are included to prevent growth of pathogens since contamination with pathogens inhibits complete development of larvae. Preferred antimicrobials are the combination of sorbic acid and methyl paraben. Sorbic acid is obtainable from Sigma Chemicals under item number S6901. Methyl paraben is available from Sigma Chemicals under item number H3647. FABCO antimicrobials did not sufficiently suppress pathogen growth and therefore do not meet the phrase "a pathogen growth suppressing amount of antimicrobial agent (s)."

In the above, standard practices for insect rearing are sometimes referred to. A reference which discloses standard practices for insect rearing is Singh, P., et al., Handbook of Insect Rearing, volumes 1 and 2, Elsevier Science Publishers B. V. Amsterdam (1988) which is incorporated herein by reference.

As indicated above, the diet here comprises a homogenous mixture of a first portion which is subjected to sterilization in an autoclave, and a second portion which is not subjected to sterilization in an autoclave. The homogenous mixture is readily prepared as follows: The ingredients which are to be sterilized in an autoclave are placed in measured amounts in a blender or other suitable mixer and are mixed therein until well-blended. The mixed ingredients are then placed in non-reactive containers, e.g., stainless steel beakers, which are placed in an autoclave wherein sterilization is carried out. The time of autoclaving should be sufficient to sterilize the ingredients but not so long that the admixture becomes too viscous to pour. The mixed autoclaved ingredients are then poured into a blender or other suitable mixer, and the second portion of ingredients, i.e., the ingredients which are not subjected to sterilization in an autoclave, are added. The ground host plant parts in the second portion can be frozen or recently thawed. After second portion of ingredients is added into the blender, mixing is carried out for a sufficient time to achieve a homogenous mixture but not for so long that the mixture cools to the point where it sets and becomes unpourable. The resulting homogenous admixture while still pourable is poured into non-reactive containers, e.g., stainless steel beakers, from where it is decanted into cups or other containers for use for placing first instar larvae on the artificial diet (step (a) in the method herein), and for incubating first instar larvae on diet (step (b) in the method herein).

The diet is readily stored at 4° C. (standard refrigerator temperature) and has been successfully stored in this way for up to a month.

The diet is useful, for example, not only in the method described below but also in less preferred or known or other methods of mass rearing of insects from larvae.

We turn now to the method herein of mass rearing of insects that feed on hard, woody plant tissue, comprising the steps of: (a) placing first instar insect larvae on an artificial diet comprising ground host plant part fed on by the larvae; (b) incubating the larvae on the diet in darkness at a temperature of 15 to 30° C. and a relative humidity of 50 to 90%; and (c) retrieving adults as they emerge.

The insects are those described above in conjunction with the diet invention herein.

The artificial diet can be that of the invention described above or other insect rearing diets comprising ground host plant part including, for example, known or less preferred or other diets comprising ground host plant part.

The insect larvae are normally and preferably placed on the diet within 24 hours of hatching.

In step (b), exposure of larvae to light should be minimized.

The insects so reared can be used, for example, for biological control agents of weeds, or in testing the effectiveness of chemicals or compounds for pest management (many beetle including weevil species are agricultural or forest pests).

We turn to the case where the method is used for mass rearing of the root-boring weevil, *Hylobius transversovittatus* for use as a biological control agent of *Lythrum salicaria* and the ground host plant root is ground purple loosestrife root. The first instar larvae for step (a) are readily obtained from eggs from an adult *Hylobius transversovittatus* colony. A mass rearing colony is maintained at Cornell University. Adults for egg production can be maintained in cages with good air circulation under close-to-natural outdoor conditions. Heat and direct sunlight should be avoided. The cages can be kept outside during the regular oviposition period of the weevil (late May to late September in Ithaca, N.Y.), for example, under a well ventilated but rain and sun protected shelter. Cage size can be, for example, approximately 30 cm per side, with approximately 50 adults kept per cage, or 45 cm by 45 cm by 50 cm with 50 to 100 adults per cage. The floor of the cages is preferably covered with crumpled paper towels as hiding places for adults. Each cage preferably contains two to four containers filled with water and sealed at the top with 2 to 4 cm thick moist florist foam. For food, 10 to 15 freshly cut purple loosestrife shoots (20 cm in length) are preferably pushed through the foam into the water. Foam and shoots are preferably replaced every week. Females lay eggs into stems and also readily accept florist foam as soil substitute for oviposition. Retrieved shoots and foams are preferably stored for 24 hours to a few days at room temperature (allowing the chorion to harden). Egg retrieval is readily carried out by dissecting the stems and lifting the eggs out with a brush and by removing eggs from the foam by scraping to expose the eggs or sieving. Hatching of the eggs to obtain first instar larvae can be carried out by placing them in small disposable petri dishes containing a thin layer of a 2% agar solution (prepared, for example, by autoclaving a flask of 2% agar: 98% water, then pouring the still-hot solution into a thin layer in the dish, i.e., to just cover the bottom, e.g., with a 2 mm layer of 2% agar solution). Eggs on agar should be kept in a warm (not hot) place with no light exposure. Most eggs hatch 4 to 14 days after being placed on the agar. It is preferred to hatch the eggs on agar rather than directly upon diet as hatching eggs on diet results in a substantial reduction in the hatch rate compared to hatching eggs on agar. Surface sterlizing of eggs, e.g., with formalin, is not preferred since it was found that such surface sterilization reduced hatch rates and resulted in increased mortality during subsequent development of larvae that successfully hatched. For step (a), first instar *Hylobius transversovittatus* larvae, normally and preferably within 24 hours of hatching, are placed on an artificial diet comprising ground purple loosestrife root. Preferably the diet comprises a homogeneous mixture of a first portion which is subjected to sterilization in an autoclave comprising by weight of the diet from 55 to 70% water, 1 to 5% agar, 1 to 5% yeast extract, 1 to 5% sucrose, 0.1 to 2% salt mix and from 1 to 5% casein, and of a second portion which is not subjected to sterilization in an autoclave, said second portion comprising by weight of the diet from 20 to 25% ground purple loosestrife root, 0.1 to 2% vitamin mix, 0.05 to 1% sorbic acid and 0.05 to 1% methyl paraben. Preferably, the first instar larvae are placed on diet which was decanted into cups as previously described and the surface of the diet is first scarified (scratched), for example, in a cross hatch pattern, to a depth of 1 to 5 mm to allow easier establishment of larvae. Preferably, each larva is transferred to diet surface under a laminar flow hood using latex gloves, using a paint brush or dissecting probe sterilized before each larva transfer with EtOH. Preferably, one or two larva are placed on diet surface in a cup containing 5 to 50 grams of diet at a distance from each other to avoid cannibalism. Increasing the number of larvae per cup was not found to result in significant differences in development times among treatments of males and females. However, adults emerging from cups with multiple larvae tended to be heavier than adults merging from cups with 1 or 2 larvae; the increased adult weight in cups with multiple larvae may be the result of cannibalism. The proportion of adults emerging decreased with increasing number of larvae per cup, e.g., for 1 ounce cups, 55% adults emerged for one larva per cup, 49% for 2 larvae per cup, 28% for 3 larvae per cup, 25% for 4 larvae per cup, and 20% for 5 larvae per cup. Preferably, the containers containing larva(e) on diet are immediately capped after transfer of larva(e) thereto. Turning now to step (b), the *Hylobius transversovittatus* larvae are incubated on diet in darkness at a temperature of 15 to 30° C. and a relative humidity of 50 to 90%. Incubation is preferably at 25 to 27° C. at a relative humidity of 60 to 80%. For incubation, the containers containing larva(e) on diet preferably are placed on trays which are positioned in incubators or in growth chambers (e.g., walk-in growth chambers from Environmental Growth Chamber of Chagrin Falls, Ohio or Conviron E-15 growth chambers from Conviron of Winnipeg, Manitoba, Canada). Humidity can be maintained simply by positioning open trays of water inside the incubator or by using a humidifier, e.g., a CP-0305 Bionaire humidifier (Bionaire Corporation, Allendale N.J.). Adults start to emerge approximately eight weeks from transfer date. Experiments were carried out using incubation at 25° C. in darkness, fluctuating between 30° C. and 20° C. with 12 hours in light and 12 hours in darkness, and fluctuating between 30° C. and 15° C. with 16 hours in light and 8 hours in darkness; superior survival rates and shortest development times were obtained at constant temperature in complete uninterrupted darkness. As indicated above, in step (c), adults are retrieved as they emerge. Adults are preferably retrieved by hand sorting. The diet and method herein reduce the development time for *H. transversovittatus* from one to two years in the field to an average of two to three months using the diet and method herein.

We turn now to the case where the method is used for the mass rearing of the root-boring weevil *Cyphocleonus achates* Fahraeus for use as a biological control agent of *Centaurea maculosa* L. The larvae are obtained from a rearing colony maintained for this purpose and the diet used comprises ground *Centaurea maculosa* root or ground *Centaurea diffusa* root. Preferably the diet comprises a homogeneous mixture of a first portion which is subjected to sterilization in an autoclave comprising by weight of the diet from 55 to 70% water, 1 to 5% agar, 1 to 5% yeast extract, 1 to 5% sucrose, 0.1 to 2% salt mix and from 1 to 5% casein, and of a second portion which is not subjected to sterilization in an autoclave, said second portion comprising by weight of the diet from 20 to 30% ground host plant root which is selected from the group consisting of ground *Centaurea maculosa* root and ground *Centaurea diffusa* root, 0.1 to 2% vitamin mix, 0.05 to 1% sorbic acid and 0.05 to 1% methyl paraben. Otherwise, the method is carried out the same as the method of mass rearing of *H. transversovittatus*. Development time for producing adult weevils is reduced from 12 months in the field to one to two months.

The invention is illustrated in the following examples.

EXAMPLE I

Diet for Mass Rearing of *Hylobius transversovittatus* Weevils

The following ingredients were measured out and placed in a one-gallon Waring blender: 1600 ml water, 52.0 g agar (Sigma #A9915), 43.4 g yeast extract (Sigma #Y1000), 65.0 g sucrose (cane sugar), 15.2 g Wesson's salt mix containing non-hydrated ferric orthophosphate (Sigma #W1374) and 69.8 g casein (Sigma #C7078). Blending was carried out for 1 minute whereupon the resulting admixture is poured into three stainless steel beakers, and the beakers were covered with aluminum foil.

The beakers were placed into a tray, and the tray was placed in a sterilmatic STM-E autoclave, manufactured by Market Forge, Everett, Mass. About one inch of water was placed in the bottom of the tray to aid in removal of any spillover. Sterilization was carried out for 20 minutes using slow exhaust for a total of 45 minutes. While the ingredient admixture in the beakers was still pourable, the autoclave was opened and the beakers were removed using autoclave gloves. Then the autoclaved mix was poured into the blender and the post autoclave ingredients were added. The post autoclave ingredients consisted of 600 g ground purple loosestrife roots, 19.2 g Vanderzant vitamin mix (Sigma #V1007), 4.3 g sorbic acid (Sigma #S6901), and 2.2 g methyl paraben (Sigma #H3647). The ground purple loosestrife root was obtained as follows: Roots were excavated at Martens Marsh, Savannah, N.Y., a 100 ha wetland on old farmland completely dominated by purple loosestrife. Rootstocks were excavated either in the fall after complete senescence, or in the spring to take advantage of maximum starch content in the roots. Roots were transported to Ithaca, N.Y., spread on a sieve and remaining soil washed off with a garden hose followed by a high pressure washer (Simpson 1500 psi, Taylor Rental, Ithaca, N.Y.). This treatment effectively removed all remaining soil particles and the root cortex. Then dead root parts and remaining woody shoots were clipped off whereupon roots were surface sterilized for 1 hour in 10% commercial bleach solution and then rinsed for 1 hour. Roots were shredded (Craftsman 5 HP, Sears, Ithaca, N.Y.) and stored at −70° C. in plastic bags. Before use in the diet, root pieces were ground in a Fritsch P-15 cutting mill (Gilson Company, Worthington, Ohio) equipped with a 1.00 mm sieve. Ground roots were either immediately used to prepare diet or stored at −70° C. in 400 g portions in re-closable plastic bags (4 mil 20 by 20 cm, Plastics Consolidated, Twinsburg, Ohio).

Blending was then carried out for 1 minute to achieve a homogeneous mixture. While the diet was still pourable (i.e., before the gel was set), it was poured back into beakers and portioned into Comet or Jet Plastic P-10 28.35 g cups (Smith Restaurant Supply, Syracuse, N.Y.), held in clear plastic tray holders (Bioserv, Frenchtown, N.J.). Each cup was filled with approximately 15 g diet and capped with Dixie PL-1 lids (Smith Restaurant Supply, Syracuse, N.Y.) and the composition in each cup congealed to a consistency of chunky peanut butter. One hundred eighty cups of diet were provided. All pouring and capping was done using latex gloves and face masks under a laminar flow hood (EdgeGard, Baker Company, Sanford, Me.) to reduce potential for contamination. Cups were stored at 4° C. in a refrigerator until needed.

EXAMPLE II

Diet for Mass Rearing of *Cyphocleonus achates* Fahraeus Weevils

The diet was made the same as the diet of Example I except that 1800 ml of water was utilized instead of 1600 ml of water and the ground root was ground *Centaurea maculosa* root or ground *Centaurea diffusa* root instead of ground purple loosestrife root.

EXAMPLE III

Mass Rearing of *Hylobius transversovittatus* Weevils

Cups of diet prepared as in Example I were used. Diet surface was scratched with a cross hatch pattern approximately ⅛ inch deep, using on EtOH sterilized probe. Then newly hatched first instar *H. transversovittatus* larvae were placed on diet surface, 1 larva per cup, using a fine paintbrush sterilized in alcohol, and the cups were capped and stored in trayholders. The trayholders containing the cups were inserted into a walk-in growth chamber (Environmental Growth Chambers, Chagrin Falls, Ohio) and incubation was carried out at 25 to 27° C. and approximately 60% relative humidity. Diet cups were checked for emergence of adults once a week, starting with the seventh week after transfer. Adults started emerging in the eighth week after transfer and continued until five months after transfer. Emerging adults were retrieved by opening the cups and removing the weevils. Use of 200 to 220 cups per week typically resulted in producing 100 weevils per week. Larval development time (to adult emergence) averaged two to three months. Sex ratio of retrieved adults was in general female biased, so there were sufficient females produced for continued egg production. Adults were collected for field release in May to September in fields of *Lythrum salicaria* L. for biological control thereof For the above where ground purple loosestrife amounted to 24.3% by weight of the diet, about 61% of larvae developed into adults. When ground purple loosestrife roots amounted to 20% of the diet, about 59% of larvae developed into adults. When purple loosestrife roots amounted to 15% of the diet, about 47% of larvae developed into adults. When purple loosestrife roots amounted to 10% of the diet, about 18% of larvae developed into adults. When purple loosestrife roots amounted to 5% of the diet, about 5% of larvae developed into adults.

EXAMPLE IV

Mass Rearing of *Cyphocleonus achates* Fahraeus Weevils

Rearing was carried out as in Example III except that the diet utilized was the diet prepared in Example II instead of the diet of Example I, and *Cyphocleonus achates* Fahraeus larvae were used rather than *H. transversovittatus* larvae. Development time (adult emergence after hatching of eggs) averaged one to two months.

Variations

Variation will be obvious to those skilled in the art. Thus, the invention is defined by the claims.

What is claimed is:

1. Diet for mass rearing of insects that feed on hard, woody plant tissue comprising a homogeneous mixture of a first portion which is subjected to sterilization in an autoclave comprising water and agar in amounts to form a gel containing the other diet components and a nutrition providing effective amount of salt mix, and of a second portion which is not subjected to sterilization in an autoclave comprising a larval development effective formulation compatible amount of ground host plant part fed on by larvae of the insects, a nutrition providing effective amount of vitamin mix and a pathogen growth suppressing amount of antimicrobial agent(s).

2. The diet of claim 1, wherein the first portion comprises by weight of the diet of 0.01 to 5% salt mix and the second portion comprises by weight of the diet of 0.1 to 40% ground host plant part, and 0.01 to 5% vitamin mix and for the antimicrobial agent(s) 0.01 to 5% sorbic acid and 0.01 to 5% methyl paraben.

3. The diet of claim 2, wherein the first portion also comprises by weight of the diet from 1 to 25% protein nutrients and from 0.5 to 15% of a sugar.

4. The diet of claim 3, wherein the protein nutrients consist by weight of the diet of 0.5 to 10% yeast extract and from 0.5 to 15% casein.

5. The diet of claim 4, wherein the first portion comprises by weight of the diet from 5 to 70% water and from 0.5 to 10% agar.

6. The diet of claim 5, wherein the first portion comprises by weight of the diet from 55 to 70% water, 1 to 5% agar, 1 to 5% yeast extract, 1 to 5% sucrose, 0.1 to 2% salt mix, and 1 to 5% casein, and wherein the second portion comprises by weight of the diet from 20 to 30% ground host plant part, 0.1 to 2% vitamin mix, 0.05 to 1% sorbic acid, and 0.05 to 1% methyl paraben.

7. The diet of claim 6, where the weevils are root feeding weevils and the ground host plant part is ground host plant root.

8. The diet of claim 7, here the weevils are *Hylobius transversovittatus,* and the ground host plant root is ground purple loosestrife root.

9. The diet of claim 7, where the weevils are *Cyphocleonos achates* Fahraeus, and the ground host plant root is selected from the group consisting of ground *Centaurea maculosa* root and ground *Centaurea diffusa* root.

10. Method of mass rearing of insects that feed on hard, woody plant tissue comprising the steps of:
    (a) placing first instar insect larvae on an artificial diet comprising ground host plant part fed on by the larvae;
    (b) incubating the larvae on the diet in darkness at a temperature of 15 to 30° C. and a relative humidity of 50 to 90%; and
    (c) retrieving adults as they emerge.

11. Method of mass rearing of the root-boring weevil *Hylobius transversovittatus* for use as a biological control agent of *Lythrum salicaria*, comprising the steps of:
    (a) placing first instar *Hylobius transversovittatus* larvae on an artificial diet as claimed in claim 8;
    (b) incubating the larvae on the diet in darkness at a temperature of 15 to 30° C. and a relative humidity of 50 to 90%; and
    (c) retrieving adults as they emerge.

12. Method of mass rearing of the root-boring weevil *Cyphocleonus achates* Fahraeus for use as a biological control agent of *Centaurea maculosa* L., comprising the steps of
    (a) placing first instar *Cyphocleonus achates* Fahraeus larvae on an artificial diet as claimed in claim 9;
    (b) incubating the larval on the diet in darkness at a temperature of 15 to 30° C. and a relative humidity of 50 to 90%; and
    (c) retrieving adults as they emerge.

* * * * *

UNITED STATES PATENT AND TRADEMARK OFFICE
CERTIFICATE OF CORRECTION

PATENT NO. : 6,293,223 B1
DATED : September 25, 2001
INVENTOR(S) : Bernd Blossey et al.

It is certified that error appears in the above-identified patent and that said Letters Patent is hereby corrected as shown below:

<u>Column 12,</u>
Line 44, change "larval" to -- larvae --.

Signed and Sealed this

Twenty-fourth Day of September, 2002

*Attest:*

*Attesting Officer*

JAMES E. ROGAN
*Director of the United States Patent and Trademark Office*